United States Patent [19]

Urgero

[11] Patent Number: 5,216,864
[45] Date of Patent: Jun. 8, 1993

[54] UNIQUE ZINC ALLOY STRIP DESIGN FOR THE INHIBITION OF MOSS AND FUNGUS

[75] Inventor: Peter P. Urgero, Richton Park, Ill.

[73] Assignee: Chicago Metallic Corporation, Chicago, Ill.

[21] Appl. No.: 786,028

[22] Filed: Oct. 31, 1991

[51] Int. Cl.⁵ ............................................. B27K 1/00
[52] U.S. Cl. ................................................. 52/515
[58] Field of Search ................. 52/173 R, 518, 101, 52/199, 276, 530, 57, 515, 516

[56] References Cited

U.S. PATENT DOCUMENTS

| | | |
|---|---|---|
| D. 20,695 | 4/1891 | Frand . |
| D. 243,695 | 3/1977 | Roux ................................ D25/80 |
| D. 263,256 | 3/1982 | Morse ............................... D25/96 |
| 3,479,130 | 11/1969 | Rapaport ............................ 21/61 |
| 3,494,727 | 2/1970 | Rapaport ............................ 21/61 |
| 5,035,079 | 7/1991 | Groves .............................. 52/105 |
| 5,119,604 | 6/1992 | Peterson et al. . |

*Primary Examiner*—Richard E. Chilcot, Jr.
*Assistant Examiner*—Beth A. Aubrey
*Attorney, Agent, or Firm*—Hill, Steadman & Simpson

[57] ABSTRACT

A metallic strip of a zinc alloy for attachment to a shingled roof to prevent or inhibit growth of fungus and moss characterized by the edges of the strip being folded over to form hems, a longitudinal crease or depression to sub-divide the strip into two longitudinally extending portions, with one portion being inserted under the shingles and being provided with openings for receiving nails for fastening the strip on the roof. Preferably, the crease has a pair of legs with reversed bends to provide a stop for limiting the insertion of the first portion under an edge of a shingle, and the other portions are provided with longitudinally extending creases and ridges to form strengthening ridges.

13 Claims, 2 Drawing Sheets

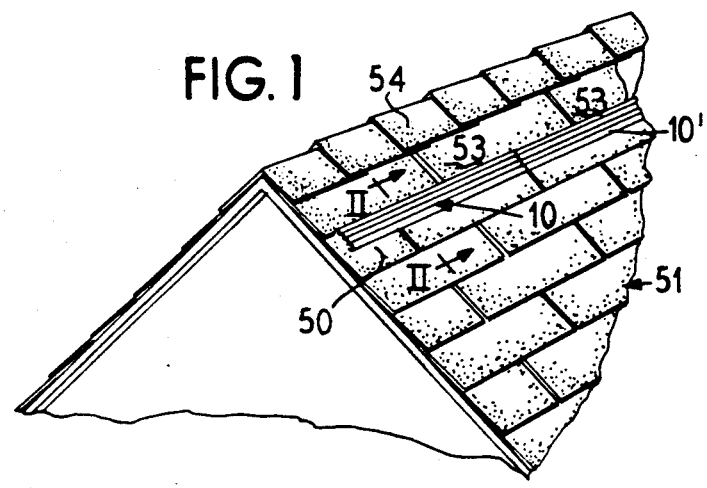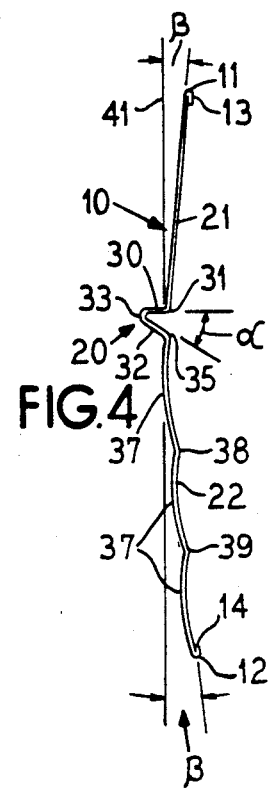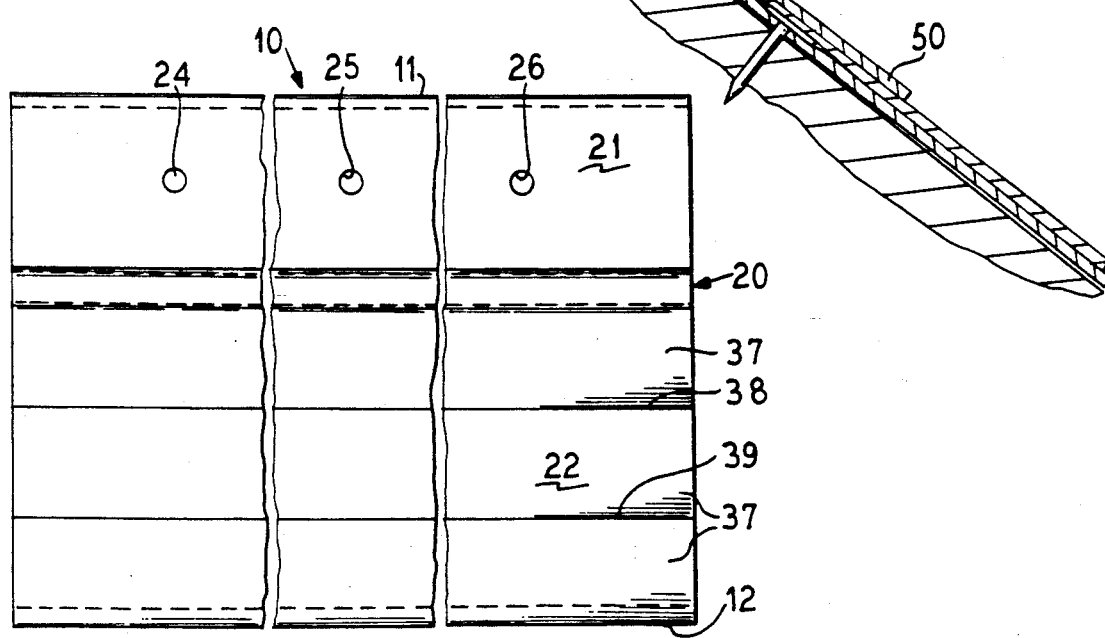

UNIQUE ZINC ALLOY STRIP DESIGN FOR THE INHIBITION OF MOSS AND FUNGUS

BACKGROUND OF THE INVENTION

The present invention is directed to a metallic strip, preferably of a solid zinc alloy, for application on a roof to inhibit the growth of moss and fungus.

Moss and/or fungus will grow on roofing materials. This growth will weaken the fibers in the shingles, whether they are wooden shingles or synthetic shingles and also when a large build-up of the moss or fungus occurs will tend to lift the shingles which will shorten the life of the roof. The growth of moss or fungus will occur on many types of roofs, including but not limited to wooden shingles, synthetic shingles, clay tile, etc.

In U.S. Pat. No. 3,494,727, whose disclosure is incorporated herein by reference thereto, it has been proposed to incorporate particles of a metallic element, which are selected from copper, lead, or zinc, into the roofing material, which element provides a biocidal ionic solution, which acts as a fungistat to inhibit the growth of a fungus or moss.

U.S. Pat. No. 3,479,130, whose disclosure is incorporated herein by reference thereto, teaches that the ions of zinc, copper and lead are microbiocidal. The patent proposes the use of a bi-metallic strip of zinc-iron or copper-lead, which is attached on a shingle roof to prevent or inhibit the growth of a fungus by the release of metal ions.

It has also been known that the use of a zinc strip placed on a roof will release zinc oxide over a period of time to inhibit the growth of moss and fungus.

Problems exist in applying such a strip in a shingled roof, which is already existing. For example, approximately ⅓ of the width of the strip is inserted under the top row of shingles adjacent the ridge cap. When inserting a strip under these shingles, it is difficult to insure that only the desired amount is inserted under the shingle to leave the desired amount exposed to release the zinc oxide fungistat. Another problem with the known strips is that they lack stiffness and, thus, become easily deformed, either during installation or subsequent to installation, due to the effects of the elements such as wind, snow, freeze and thaw cycles, etc.

SUMMARY OF THE INVENTION

The object of the present invention is to provide an improved and unique design employing the use of a solid zinc alloy strip to inhibit the growth of moss and fungus on a roof, which strip can be easily inserted under a row of existing shingles to the desired depth or amount and has adequate stiffness.

To accomplish these goals, the invention is directed to a metallic strip for releasing material to inhibit the growth of moss and fungus, said strip having each of the lateral edges folded over to form a hem, each strip having openings formed adjacent one of the edges to enable passage of a fastener for securing the strip on a roof structure, and means forming a line adjacent the opening to enable a determination of the depth of penetration of the strip under a row of shingles. Preferably, the metallic strip is of a solid zinc alloy and has a roughened surface to reduce reflection, to increase rigidity and to hold water on the surface of the strip. In addition, it is desirable for the strip to have additional means for increasing rigidity, including a plurality of longitudinally extending ribs, with one of the ribs forming the means for forming a line.

In the preferred embodiment, the means for forming a line includes an upstanding rib which also forms a shingle stop to limit the depth of penetration of the strip under a row of shingles. To insure that the strip snugly engages the shingle therebelow, the preferred embodiment of the strip is also provided with a curved cross sectional configuration to provide a spring action to hold or press the strip against the shingle as it is secured by fasteners passing through the openings adjacent the one edge.

Other advantages and features of the invention will be readily apparent from the following description of the preferred embodiments, the drawings and claims.

BRIEF DESCRIPTION OF THE DRAWINGS

FIG. 1 is a partial perspective view of a top of a shingled roof having a ridge cap with a strip for inhibiting the growth of moss inserted adjacent the upper row of shingles;

FIG. 2 is a cross sectional view taken along the lines II—II of FIG. 1 with portions in elevation for purposes of illustration showing the mounting of the strip in accordance with the present invention;

FIG. 3 is a plan view of the preferred embodiment of the strip in accordance with the present invention;

FIG. 4 is an end view of the preferred embodiment of FIG. 3 in an unassembled state;

DESCRIPTION OF THE PREFERRED EMBODIMENTS

Figure 5:
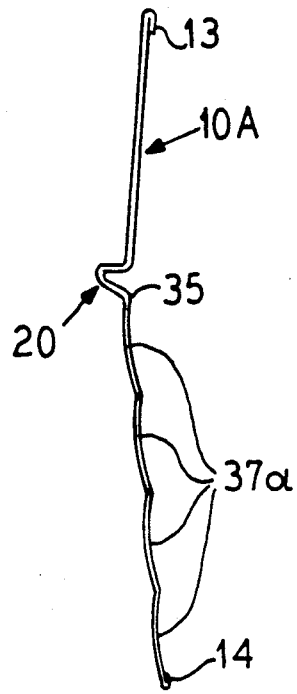
FIG. 5 is an end view of a modification of the strip in accordance with the present invention.

The principles of the present invention are particularly useful when incorporated in a metallic strip, generally indicated at 10 in FIGS. 1–4. The strip 10, as illustrated in FIGS. 3 and 4, has a length of approximately 36 inches, with two lateral edges 11 and 12 provided with a reversed bend to form hems 13 and 14, respectively, which have a double-thickness (see FIG. 4). The strip 10 has means, generally indicated at 20, for forming a line (see FIG. 4) that sub-divides the strip into approximately two longitudinal portions 21 and 22, with the portion 21 being approximately half the width of the portion 22. In the portion 21, approximately midway between the means 20 for forming a line and the lateral edge 11, three openings 24, 25 and 26 are formed, with the openings 24 and 26 being spaced inward from the adjacent ends by approximately one inch and the opening 25 being at the mid-point of the strip, or approximately 18 inches inward from each end.

The means 20, as best illustrated in FIG. 4, is formed by an upstanding ridge comprising a leg 30 formed by a substantially right angle bend 31. The leg 30 is connected to a leg 32 by a reversed bend 33 so that the leg 30 forms an angle α of approximately 30° with the leg 32. The leg 32 is connected to the portion 22 by a bend line 35.

To increase the stiffness, the portion 22 is illustrated as being provided with three longitudinally extending ribs 37, which are of equal size and are formed by the bend line 35 plus bend lines or creases 38 and 39.

Preferably, when forming the strip 10, the bends, such as the bend line 35 and the bend at 31, are such that the portion 21 is offset and forms an angle of approximately 95° to the leg 30 so that it forms an angle $\beta$ of approximately 5° with a plane 41 which extends perpendicular to the plane of the leg 30. The portion 22 is also offset and forms an angle $\beta$ of approximately 5° to this plane 41. Thus, the strip has a concave configuration in a side opposite the legs 30, 32. The purpose of these offset positions is so that when the strip 10 is secured on a shingle 50 of a roof, generally indicated at 51, by fasteners, such as nails 52, which pass through the openings 24, 25 and 26, the nails will hold the strip 10 flat on the shingles with a spring-like action to insure that the edge 12 is urged against the surface of the shingle 50.

When the strips 10 are inserted on the roof 51, they are preferably inserted under the first row of shingles 53 (FIG. 1), which is immediately adjacent the ridge cap 54. As illustrated in FIG. 2, the means 20 act as a shingle stop to limit the depth of insertion of the portion 21 under the edge of the shingles 53. It is noted that the height of the leg 30 is selected to be less than the thickness of the shingle so that an upper surface 55 of the shingle is above the return bend 33 so that water flowing along on the surface 55 will pass over the stop formed by the means 20 without forming a dam. While the strips 10 are illustrated as being inserted under the top most row of shingles 53, they could also be inserted under an edge of the ridge cap 54. In addition if the roof has an obstruction such as a chimney or a dormer, then additional strips are also mounted at the base of the obstruction.

Preferably, before forming the strip, its exposed surface has been given a roughened finish, such as by passing through embossing rolls to give it a stucco tureturetype configuration, which will reduce the reflectivity of the strip, will increase the rigidity of the strip, and will increase the contact surfaces with water. As illustrated in FIG. 2, the provision of the hem, such as 13, facilitates the insertion of the portion 21 under the shingles, such as 53. The hems 13 and 14 improve the safe handling of the strip 10 because the strip has no exposed sharp edges. The hem 14 also increases the rigidity adjacent the edge 12. As mentioned above, the 5° offset of the portions 21 and 22 from the plane 41 insures a snug fit, due to spring-like action against the shingle when the strip 10 is secured by the fasteners, such as nails 52. In addition to providing a shingle stop, the means 20 may also act to help prevent wind from catching underneath the edges of the shingles 53. The use of the openings, such as 24, 25 and 26, for the nails insures that the strip will not be unduly bent or deformed installation. Thus, a strip 10, such as illustrated in FIG. 1 will have a smooth transition to the next strip 10', which is adjacent thereto.

A first modification of the strip 10 is illustrated by the strip, generally indicated at 10A in FIG. 5. In this modification, instead of having three longitudinally extending ribs, four longitudinal ribs 37a are provided, which have less width than the ribs 37 of the embodiment of FIG. 4. The remaining portions of the strip 10A are the same as in the embodiment of FIGS. 3 and 4.

Figure 6:
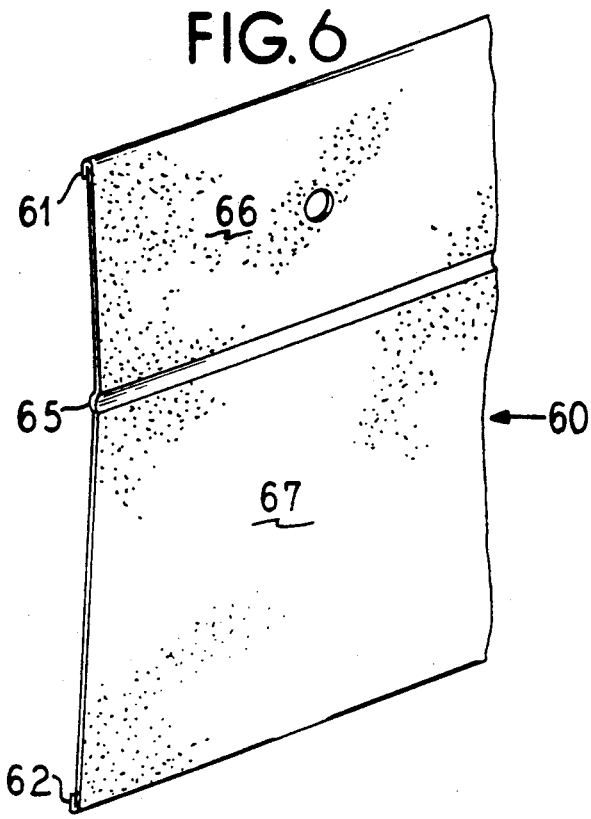
FIG. 6 is a perspective view of an embodiment of the strip in accordance with the present invention.
Figure 7:
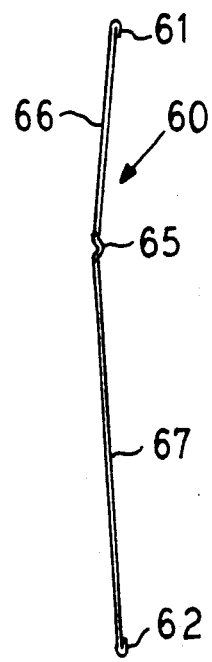
FIG. 7 is an end view of the strip of FIG. 6.

As mentioned above, problems with fungus and moss occur in many types of roof materials. Thus, in some instances, when utilizing tile roofs or roofs utilizing rough wooden shakes, the presence of the stop means 20 having a rather deep ridge provides sufficient stiffness to limit the molding of the strip to the contour of the tile or wooden shakes. An embodiment illustrated by a strip, generally indicated at 60 in FIGS. 6 and 7, can be used. In this embodiment, the strip is provided with reversed bends 61 and 62 to form hems along the lateral edges, a means 65 comprising a small indented groove or depression is provided to form a line to divide the strip into portions 66 and 67 and to provide a line for gauging the depth of insertion of the portion 66 beneath an edge of the shingle. In addition, the two portions 66 and 67 are illustrated as having the stucco or roughened surface to reduce reflections and these portions 66 and 67, if desired, can be offset relative to a plane by approximately 5° so that when mounted by nails passing through openings, such as 68, they will have a snug engagement of the shingle, due to the compression of their spring-like concave cavity. Due to the fact that neither the portions 66 or 67 is provided with reinforcing grooves, the strip can be easily molded to the contour of the roofing material, such as tiles or wooden shakes.

Figure 8:
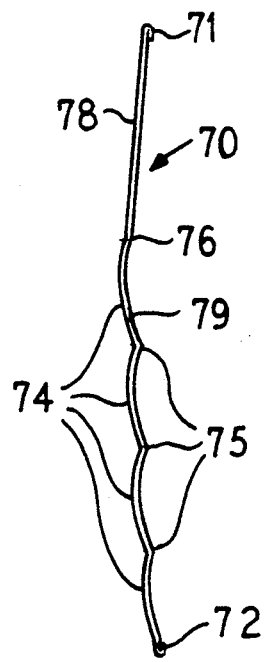
FIG. 8 is an end view of yet another embodiment of the strip in accordance with the present invention.

Another embodiment is generally indicated by the strip 70 in FIG. 8. In this embodiment of the strip 70, the lateral edges are provided with reversed bends to form hems 71 and 72. Adjacent the hem 72, the strip is provided with four longitudinally extending ribs 74, which are formed by three crease lines 75 and an upper crease line 76. The upper crease line 76 also acts as means for forming a line to separate a portion 78 from a portion 79, which portion 79 contains the ribs 74. The portion 78, like the portion 66 in the embodiment of the strip 60, contains the openings for nailing or securing the strip on a roof.

In both the embodiments 60 and 70, the strip is inserted with the portions 66 or 78 inserted underneath the edge of the row of shingles, with the edge of the shingle being brought up to the line formed either by the depression 65 or the crease 76. As in the previous two embodiments, due to the slight offset, nailing or securing of the strip 60 or 70 on the shingle will cause the strip to snugly engage the upper surface of the shingle.

Each of the strips, as mentioned above, has a length of approximately 36 inches and has a width of approximately 3 inches, with the portions, such as 21, 66 or 78, being approximately 1 inch. The strips are preferably made of zinc alloy, which contains between 0.6% and 1% copper and traces of other contaminants, such as aluminum, titanium, iron, lead and cadmium in amounts less than 0.01% max and have a thickness of approximately 0.01 inch, which strips are rolled to the forms illustrated. It would be possible to use a steel strip which after being formed was either hot dipped or coated with zinc. However, it is believed that a zinc coated steel strip would not last as long as the preferred solid zinc alloy strip.

Although various minor modifications may be suggested by those versed in the art, it should be understood that I wish to embody within the scope of the patent granted hereon all such modifications as reasonably and properly come within the scope of my contribution to the art.

I claim:

1. A metallic strip for releasing material for inhibiting the growth of moss and fungus, said strip comprising a solid zinc alloy strip having a length with lateral edges extending therealong, said strip having reversed bends along the lateral edges to form hems, said strip having a roughened surface, means for forming a line extending the length of the strip to subdivide the strip into a first portion and a second portion, with the second portion having a greater width than the first portion, said strip having openings formed in the first portion for receiving fastening means for securing the strip in a roof structure.

2. A metallic strip according to claim 1, wherein the means for forming a line is formed by a plurality of longitudinally extending bends to form an upstanding ridge which acts as a shingle stop to limit the depth of insertion of the first portion under the edge of a shingle.

3. A metallic strip according to claim 2, wherein the plurality of longitudinally extending bends form two longitudinally extending legs which extend at approximately an angle of 30° to each other, with the height of the legs being less than the thickness of the shingle.

4. A metallic strip according to claim 3, wherein the first and second portions are offset relative to a plane so that the strip has a concave configuration on a surface opposite the shingle stop.

5. A metallic strip according to claim 4, wherein the second portion has a plurality of longitudinally extending creases to form a plurality of longitudinally extending ribs to increase the rigidity of said strip.

6. A metallic strip according to claim 1, wherein the means for forming a line is a crease.

7. A metallic strip according to claim 6, wherein the second portion has means for increasing rigidity, including a plurality of additional longitudinal creases forming longitudinally extending ribs.

8. A metallic strip according to claim 1, wherein the strip has ends and the openings are located with one adjacent each end of the strip and one at a mid-point of the strip.

9. A metallic strip according to claim 8, wherein the means for forming a line comprises a plurality of longitudinally extending bends forming an upstanding ridge which extends the length of the strip and acts as a shingle stop to limit the depth of insertion of the first portion under the edge of a shingle.

10. A metallic strip according to claim 8, wherein the means for forming a line is a crease.

11. A metallic strip for releasing material to inhibit the growth of fungus, said strip having a length with lateral edges extending therealong, said strip having reversed bends along the lateral edges to form hems, said strip having a roughened surface, means for forming a line extending the length of the strip to subdivide the strip into a first portion and a second portion, with the second portion having a greater width than the first portion, said strip having openings formed in the first portion for receiving fastening means for securing the strip in a roof structure.

12. A metallic strip according to claim 11, wherein the metallic strip has zinc surfaces.

13. A metallic strip according to claim 11, wherein the metallic strip is a solid zinc alloy strip.

* * * * *